US00PP36150P2

(12) United States Plant Patent
Kerley

(10) Patent No.: US PP36,150 P2
(45) Date of Patent: Sep. 24, 2024

(54) ***BEGONIA* PLANT NAMED 'KERBESPIPPLE'**

(50) Latin Name: *Begonia tuberhybrida*
Varietal Denomination: KERBESPIPPLE

(71) Applicant: Timothy Edward Kerley, Willingham (GB)

(72) Inventor: Timothy Edward Kerley, Willingham (GB)

(73) Assignee: Kerley & Co Ltd. (GB)

( * ) Notice: Subject to any disclaimer, the term of this patent is extended or adjusted under 35 U.S.C. 154(b) by 0 days.

(21) Appl. No.: 18/416,178

(22) Filed: Jan. 18, 2024

(51) Int. Cl.
*A01H 5/02* (2018.01)
*A01H 6/18* (2018.01)

(52) U.S. Cl.
USPC ..... Plt./344

(58) Field of Classification Search
USPC ..... Plt./343, 344
See application file for complete search history.

*Primary Examiner* — Susan McCormick Ewoldt
(74) *Attorney, Agent, or Firm* — Cassandra Bright

(57) ABSTRACT

A new and distinct cultivar of *Begonia tuberhybrida* plant named 'KERBESPIPPLE' is disclosed, characterized by large, fragrant, double white flowers with a pink flush. Plants are mounding to semi-trailing, free-flowering, with excellent garden performance. The new variety is a *Begonia*, normally used as an ornamental garden or container plant.

2 Drawing Sheets

Latin name of the genus and species: *Begonia tuberhybrida.*

Variety denomination: 'KERBESPIPPLE'.

BACKGROUND OF THE INVENTION

The new cultivar is the product of a planned breeding program. The new variety originated as the result of a crossing performed during September of 2015 of *Begonia* 'Fragrant Blush'(unpatented) with the pollen parent, *Begonia tuberhybrida* '15-501-7'(unpatented). The selection of the new variety was made in June 2016, by the inventor at a research greenhouse located in Cambridge, UK.

Asexual reproduction of the new cultivar 'KERBESPIPPLE' was first performed at a research greenhouse located in Cambridge, UK by terminal vegetative cuttings during October 2016. 'KERBESPIPPLE' has since produced several generations by vegetative cuttings and has shown that the unique features of this cultivar are stable and reproduced true to type.

SUMMARY OF THE INVENTION

The cultivar 'KERBESPIPPLE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBESPIPPLE.' These characteristics in combination distinguish 'KERBESPIPPLE' as a new and distinct *Begonia tuberhybrida* cultivar:

1. Large double flowers.
2. Fragrant flowers.
3. Free-flowering.

4. Excellent garden performance.
5. White flowers with a flush of pink.

PARENT COMPARISONS

Plants of the new cultivar 'KERBESPIPPLE' are similar to plants of the seed parent variety in most horticultural characteristics. However, plants of the new cultivar 'KERBESPIPPLE' differ in the following:

1. Flowers of the new variety are fragrant, while flowers of the seed parent have no fragrance.
2. Flowers of the new variety are double, while flowers of the seed parent are semi-double.
3. Growth habit of the new variety is mounding to semi-trailing, while the growth habit of the seed parent is upright.

Plants of the new cultivar 'KERBESPIPPLE' are similar to plants of the pollen parent variety in most horticultural characteristics. However, plants of the new cultivar 'KERBESPIPPLE' differ in the following:

1. Plants of the new variety are not as free-flowering as plants of the pollen parent.
2. Plants of the new variety produce fewer branches than plants of the pollen parent.
3. Plants of the new variety are less vigorous than plants of the pollen parent.

COMMERCIAL COMPARISON

Plants of the new cultivar 'KERBESPIPPLE' are similar to plants of the commercial variety, *Begonia* 'Kerbespicit', U.S. Plant Pat. No. 29,308, in most horticultural characteristics. However, plants of the new cultivar 'KERBESPIPPLE' differ in the following:

1. Flowers of the new variety are larger than flowers of this comparator.
2. Flower color of the new variety is white with a pink flush, while the flower color of this comparator is yellow.

3. Plants of the new variety branch more abundantly than plants of this comparator.
4. Plants of the new variety are less compact than plants of this comparator.
5. Flower habit of the new variety is more pendulous than the flower habit of this comparator.
6. The new variety produces more flowers than this comparator.

BRIEF DESCRIPTION OF THE PHOTOGRAPHS

The present invention of a new and distinct variety of *Begonia* is shown in the accompanying photographs, the colors being as nearly true as possible with color photographs of this type.

DETAILED BOTANICAL DESCRIPTION

Figure 1:
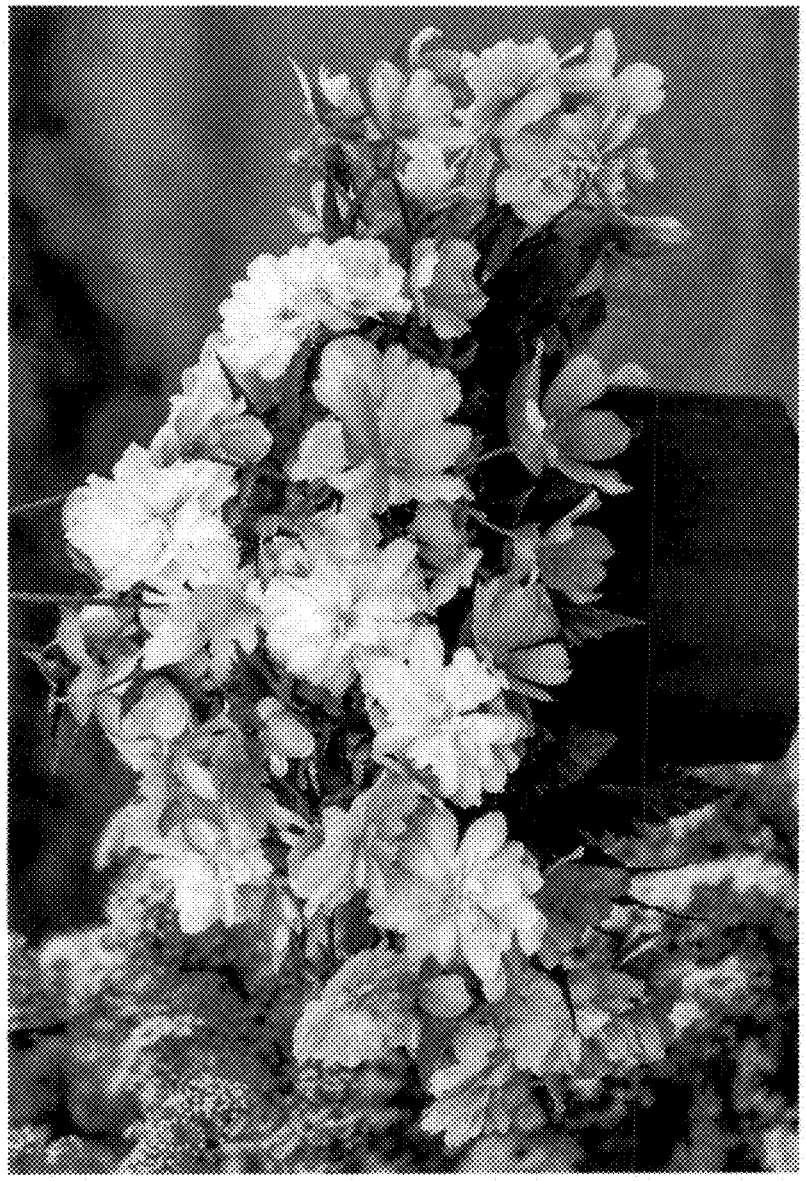
FIG. 1 illustrates a plant of approximately 6 months in a 20 cm pot
Figure 2:
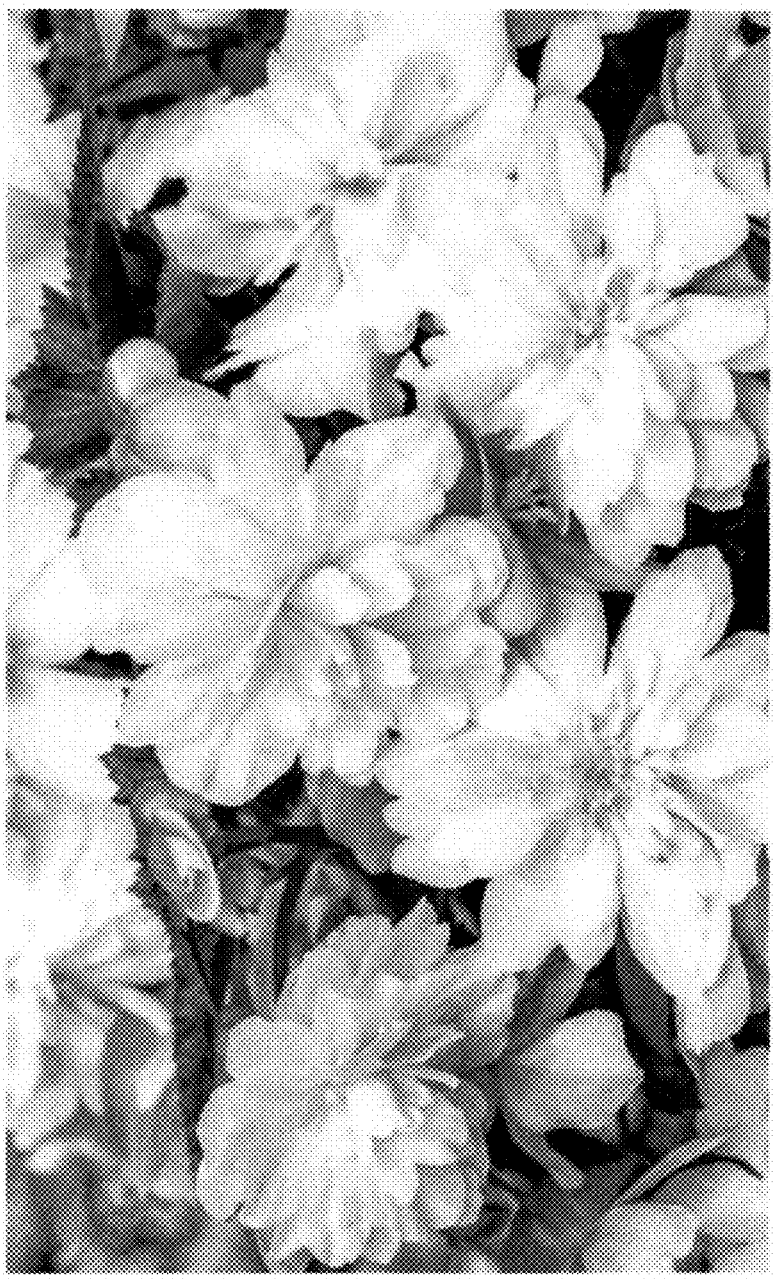
FIG. 2 illustrates a close up of the flowers

In the following description, color references are made to The Royal Horticultural Society Colour Chart 2001 except where general terms of ordinary dictionary significance are used. The following observations and measurements describe 'KERBESPIPPLE' plants grown in a commercial controlled greenhouse in Cambridge, United Kingdom. Measurements and numerical values represent averages of typical plant types.

Botanical classification: *Begonia tuberhybrida* 'KERBESPIPPLE'.

Age of plant described: Approximately 16 weeks.

Container of plant described: 11 liter.

PROPAGATION

Type of propagation typically used: Softwood stem cuttings.

Time to develop roots: About 14 days at approximately 22° C.

Time to develop a rooted liner: About 18 days at approximately 22° C.

Root description: Fibrous, fine, well branched. White and tan, not accurately measured with The R.H.S. chart.

PLANT

Growth habit: Mounding to semi-trailing.

Height: 19 cm.

Plant spread: 28 cm.

Growth rate: Moderately vigorous.

Branching characteristics: Well branched.

Characteristics of primary lateral branches:

*Form*.—Round.

*Length*.—18 cm.

*Diameter*.—1.1 cm.

*Color*.—RHS Greyed-Green 197A at base changing to 197B up the stem. Overlaid with Red 181A, more prominent up the stem.

*Texture*.—Slightly pubescent.

*Aspect*.—Upwards and outwards.

Internode length: 2.7 cm.

FOLIAGE

*Arrangement*.—Alternate.

*Quantity*.—7 per primary lateral branch.

*Length*.—10.5 cm.

*Width*.—5.8 cm.

*Shape of blade*.—Asymmetrical.

*Apex*.—Acute.

*Base*.—Oblique.

*Margin*.—Double serrate, undulating slightly.

*Texture of top surface*.—Smooth, both surfaces.

*Aspect*.—Mainly flat. Weak upward curve to overall leaf.

*Color*.—Young foliage, upper side: RHS Yellow-Green 147A. Young foliage, under side: RHS Red 183C to 183A. Mature foliage, upper side: RHS Green NN137A. Mature foliage, under side: RHS Yellow-Green 148B.

*Venation*.—Type: Palmate. Color: Young foliage, upper side: RHS Yellow-Green 146B. Young foliage, under side: RHS Red 183C. Mature foliage, upper side: RHS Yellow-Green 146A. Mature foliage, under side: RHS Yellow-Green N148B.

*Petiole*.—Length: 3.5 cm. Diameter: 0.4 cm. Color: Near RHS Greyed-Orange 176C and 176D. Texture: Pubescent.

*Stipule Description*.—Usually 1 per leaf, occasionally 2. Length: 0.6 cm. Diameter: 0.2 cm. Color: Near RHS Yellow-Green 146D. Texture: Glabrous.

FLOWER

Flowering season: May to September in Cambridge, UK.

Flower type and habit: Fully double male flowers, single female flowers present.

Quantity: About 18 per plant; 3 per peduncle.

Persistent or self-cleaning: Self-Cleaning.

Fragrance: Citrus.

Bud:

*Shape*.—Flattened, hemispherical.

*Length*.—1.5 cm.

*Diameter*.—1.6 cm.

*Color*.—RHS Yellow 1C, blushed Purple-Pink 65C in some places.

Flower size:

*Male*.—8 cm.

*Female*.—5.5 cm.

Tepals:

*Quantity*.—Male: Average 55 double per flower. Female: 5 single per flower.

*Arrangement*.—Rosette.

*Length*.—Male: 3.7 cm. Female: 2.5 cm.

*Width*.—Male: 4 cm. Female: 4 cm.

*Shape*.—Oval.

*Apex*.—Irregularly obtuse.

*Base*.—Broad tapered.

*Margin*.—Entire.

*Texture, upper and lower surfaces*.—Glabrous.

*Color*.—Male Young Flower: Base RHS Yellow 19A, changing to 19D, flushed Purple-Pink 65C. Male Mature Flower: Upper side: RHS Yellow 162A at base changing to White NN155B, flushed Purple-Red 70D. Lower side: RHS Yellow 162A at base changing to White NN155A, flushed Purple-Red

65A. Female Young Flower: RHS White NN155A, flushed Purple-Pink 65A at edge. Female Mature Flower: Upper side: RHS Red-Orange 35B at base changing to Purple-Red 65C, flushed Red 47D. Lower side: RHS Red 47D at base changing to Purple-Red 62C, flushed Red 47C.

Flower bracts:

*Arrangement*.—Opposite.

*Quantity per flower*.—2.

*Shape*.—Oval.

*Length*.—1.5 cm.

*Diameter*.—1.1 cm.

*Apex*.—Obtuse.

*Margin*.—Entire.

*Texture*.—Glabrous.

*Color*.—Near RHS Red-Orange 34C.

REPRODUCTIVE ORGANS

Androecium: Not observed.

Pistil: 3 sections of style with curled edges forming twirls for the stigma. Color: RHS Yellow 12A on new flower; 13A on mature flower.

OTHER CHARACTERISTICS

Seeds and fruits: Not observed to date.

Disease/pest resistance: Neither resistance nor susceptibility to diseases or pests of *Begonia*has been observed in this variety.

Temperature tolerance: Not observed.

What is claimed is:

1. A new and distinct cultivar of *Begonia* plant named 'KERBESPIPPLE' as herein illustrated and described.

* * * * *